US009364666B2

(12) United States Patent
Chen

(10) Patent No.: US 9,364,666 B2
(45) Date of Patent: Jun. 14, 2016

(54) METHOD OF USING A GASTROINTESTINAL STIMULATOR DEVICE FOR DIGESTIVE AND EATING DISORDERS

(75) Inventor: Jianfeng Chen, Tulsa, OK (US)

(73) Assignee: Transtimulation Research, Inc., Oklahoma City, OK (US)

(*) Notice: Subject to any disclaimer, the term of this patent is extended or adjusted under 35 U.S.C. 154(b) by 1266 days.

(21) Appl. No.: 11/800,540

(22) Filed: May 7, 2007

(65) Prior Publication Data

US 2008/0281374 A1 Nov. 13, 2008

(51) Int. Cl.
A61N 1/372 (2006.01)
A61N 1/32 (2006.01)
A61N 1/36 (2006.01)
A61N 1/375 (2006.01)

(52) U.S. Cl.
CPC ........... *A61N 1/36007* (2013.01); *A61N 1/3756* (2013.01)

(58) Field of Classification Search
USPC ................ 607/40, 41, 46, 116, 133, 134, 138
See application file for complete search history.

(56) References Cited

U.S. PATENT DOCUMENTS

| | | | |
|---|---|---|---|
| 5,423,872 A * | 6/1995 | Cigaina | 607/40 |
| 5,690,691 A | 11/1997 | Chen et al. | |
| 6,826,428 B1 | 11/2004 | Chen et al. | |
| 7,054,690 B2 | 5/2006 | Imran | |
| 2002/0055761 A1 * | 5/2002 | Mann et al. | 607/41 |
| 2002/0198470 A1 * | 12/2002 | Imran et al. | 600/587 |
| 2003/0144708 A1 * | 7/2003 | Starkebaum | 607/40 |
| 2004/0015201 A1 * | 1/2004 | Greenstein | 607/40 |
| 2004/0088022 A1 | 5/2004 | Chen | |
| 2005/0021101 A1 * | 1/2005 | Chen et al. | 607/40 |
| 2005/0209653 A1 * | 9/2005 | Herbert et al. | 607/40 |
| 2005/0222637 A1 | 10/2005 | Chen | |
| 2005/0222638 A1 | 10/2005 | Foley et al. | |
| 2006/0020278 A1 * | 1/2006 | Burnett et al. | 606/153 |
| 2006/0036293 A1 * | 2/2006 | Whitehurst et al. | 607/40 |
| 2006/0247719 A1 * | 11/2006 | Maschino et al. | 607/40 |
| 2007/0016262 A1 * | 1/2007 | Gross et al. | 607/40 |
| 2007/0027492 A1 * | 2/2007 | Maschino et al. | 607/40 |
| 2007/0123809 A1 * | 5/2007 | Weiss et al. | 601/84 |
| 2008/0108868 A1 * | 5/2008 | Swain et al. | 600/104 |

OTHER PUBLICATIONS

Capsule Endoscopy; www.givenimaging.com/cultures/en-US/given/english.

(Continued)

*Primary Examiner* — Carl H Layno
*Assistant Examiner* — Jennifer Ghand
(74) *Attorney, Agent, or Firm* — Dunlap Codding, P.C.

(57) ABSTRACT

Methods of using a stimulator device in the treatment of: gastrointestinal disorders such as dysphagia, gastroesophageal reflux diseases, functional dyspepsia, gastroparesis, postoperative ileus, irritable bowel syndrome, constipation, diarrhea, fecal incontinence, nausea and vomiting; gastrointestinal obstruction or pseudo-obstruction; pain and/or discomfort related to visceral organs; eating disorders, such as obesity, binge eating, bulimia, anorexia, and chemotherapy-induced emesis or emesis of other origin. The stimulator device generally includes a housing, at least two electrodes, and a pulse generator. The housing has an exterior surface and an interior surface defining a sealed interior space. The housing is constructed of bio-compatible materials and sized and shaped for transport through the gastrointestinal tract.

9 Claims, 3 Drawing Sheets

(56) References Cited

OTHER PUBLICATIONS

Smartpill; www.smartpillcorp.com.
Zhang, J, J.D.Z. Chen; Systematic Review; Applications and Future of Gastric Electrical Stimulation; Alimentary Pharmacology & Therapeutics 2006; pp. 991-1002.

Shi Liu, M.D., et al., Therapeutic Potential of Duodenal Electrical Stimulation for Obesity: Acute Effects on Gastric Emptying and Water Intake; American Journal of Gastroenterology 2005; pp. 792-796.

* cited by examiner

METHOD OF USING A GASTROINTESTINAL STIMULATOR DEVICE FOR DIGESTIVE AND EATING DISORDERS

BACKGROUND OF THE INVENTION

Gastrointestinal stimulation, or pacing, was advocated as a possible treatment for gastric motor dysfunction as early as 1963. Experimentation in the late 1960s and early 1970s, began to demonstrate the significance of gastrointestinal myoelectrical activity and its relation to contractile activity.

Stimulation of the gastrointestinal tract has been shown to be able to alter, inhibit, or excite gastrointestinal motor functions, activate intrinsic and extrinsic neuronal pathways and/or solicit hormonal/peptide releases. Because of these characteristics, gastrointestinal stimulation has been shown to be effective in normalizing gastric dysrhythmia, accelerating gastric emptying, reducing symptoms such as nausea and vomiting, and even used as in the treatment of chemotherapy-induced emesis. Recently, gastrointestinal stimulation has also been studied as a therapy for obesity.

Obesity is a growing public health problem with a lack of satisfactory treatments. Recent research seems to suggest that gastrointestinal stimulation may delay gastric emptying and thereby assist in prolonging meal intervals and reducing frequent snacking without the risks and complications of surgery. Fluid intake may also be induced by gastrointestinal stimulation so as to assist in reducing appetite, for example, by reducing the capacity for accommodating food within the gastrointestinal tract as detailed in "Therapeutic Potential of Duodenal Electrical Stimulation for Obesity: Acute Effects on Gastric Emptying and Water Intake" by Shi Liu, Xiaohua Hou, and J. D. Z. Chen in *American Journal of Gastroenterology*, Volume 100, pages 792-796 (2005) that is hereby incorporated by reference in its entirety.

Several devices have been developed to provide for gastrointestinal stimulation. See GASTROINTESTINAL PACEMAKER HAVING PHASED MULTIPOINT STIMULATION (U.S. Pat. No. 5,690,691), GASTROINTESTINAL ELECTRICAL STIMULATION (U.S. Pat. No. 6,826,428), SENSOR BASED GASTROINTESTINAL ELECTRICAL STIMULATION FOR THE TREATMENT OF OBESITY OR MOTILITY DISORDERS (U.S. Patent Publication No. 2005/0222638), PROCESS FOR ELECTROSTIMULATION TREATMENT OF MORBID OBESITY (U.S. Patent Publication No. 2004/0088022), TACHYGASTRIAL ELECTRICAL STIMULATION (U.S. Patent Publication No. 2005/0222637), each of which is hereby incorporated by reference in its entirety. However, research into the practical implementations of gastrointestinal stimulation has been hindered by the invasive nature of the devices of previous gastrointestinal stimulation therapies. For example, implantable stimulator devices, currently available for treating gastric disorders and diseases, require invasive abdominal surgery that increases risks and complications associated with the procedure.

Accordingly, a less invasive means and method for delivering gastrointestinal stimuli will provide more convenient and desirable treatment options for potentially numerous disorders and diseases.

BRIEF SUMMARY OF THE INVENTION

In one embodiment, the present invention is related to a stimulator device for providing stimulation to the gastrointestinal intestinal tract of a user, such as a human, or other type of mammal. In general, the stimulator device is provided with a housing, at least two electrodes, and a pulse generator. The housing has an exterior surface and an interior surface defining a sealed interior space. The housing is constructed of biocompatible material and sized and shaped for transport through the gastrointestinal tract of the user. A portion of each of the at least two electrodes is disposed on the exterior surface of the housing. The pulse generator is disposed in the interior space of the housing and delivers pulses to the electrodes to stimulate the gastrointestinal tract of the user.

In one version of the invention, the housing is formed by the at least two electrodes, and an insulating material separating such electrodes. In this regard, the housing is partially formed of a polymer material. In one embodiment, the insulating material, such as the polymer material, is non-digestible within the gastrointestinal tract of the user.

As discussed above, the housing is sized and shaped for transport through the gastrointestinal tract of the user. Typically, the housing is capsule shaped, although other shapes can be used so long as the housing is sized and shaped for transport through the gastrointestinal tract.

In general, the pulse generator delivers pulses to the electrodes so that the electrodes deliver the pulses to the gastrointestinal tract of the user. The pulses can be provided in a variety of different manners, such as intermittent pulses, continuous pulses, and/or a train of intermittent and/or continuous pulses. Such pulses can be delivered via the at least two electrodes to the gastrointestinal tract via any suitable medium, such as electricity, acoustic waves, radiation, photons, or the like.

In one embodiment, the device is further provided with a controller for regulating the pulses to the electrodes. The controller can either be external to the housing and in communication with the pulse generator, or internal to the housing. When the controller is external to the housing, such controller can communicate with the pulse generator via any suitable manner such as electromagnetic waves, inductive coupling, or the like. In one preferred embodiment, the controller electromagnetically controls the pulse generator.

Preferably, the controller is programmed with a stimulation parameter either prior to or during transport of the housing through the gastrointestinal tract. The stimulation parameter is utilized by the controller to control the pulse generator such that the pulse generator delivers pre-determined types of pulses to the electrodes. Stimulation parameters can include frequency, pulse width, amplitude, and the like. It should be understood that the stimulation parameters utilized to control the controller can be modified according to the desires of the designer and/or the patient.

In one embodiment, the device can be further provided with a sensor system for detecting environmental conditions around the housing. The environmental conditions can be used to determine the location of the device within the gastrointestinal tract of the user and such information received from the sensor system can be fed back to the controller to provide feedback to help control the controller. The sensor system can include one or more sensors for sensing a variety of different types of environmental factors which may be surrounding the housing of the device. For example, mechanical contractions, pressure, tension, electrical signals, temperature, pH or the like.

In one embodiment, the device further comprises a power source for supplying power to the pulse generator. The power source can be implemented in a variety of manners, such as a battery supported by the housing and supplying power to the pulse generator, or a separate device provided external to the user which provides power to the pulse generator through a wireless mechanism, such as inductive loop coupling.

In another aspect, the present invention is directed to a method of using a stimulator device to emit a medium for treatment of a gastrointestinal disorder, such as weakened or exaggerated pressure, tone or contractions, gastric dysrhythmia, nausea, or vomiting. In general, the stimulator device is provided to a patient or user. The stimulator device includes a pulse generator and at least a pair of electrodes with at least a portion of the pulse generator and the electrodes encapsulated or supported by housing. The stimulator device is placed in the gastrointestinal tract of the patient, such as by oral administration or rectal administration or any fistulas or open holes connected to the gastrointestinal tract. Once the stimulator device is inside the gastrointestinal tract, the stimulator device delivers pulses to the gastrointestinal tract.

BRIEF DESCRIPTION OF THE SEVERAL VIEWS OF THE DRAWINGS

So that the above recited features and advantages of the present invention can be understood in detail, a more particular description of the invention, briefly summarized above, may be had by reference to the embodiments thereof that are illustrated in the appended drawings. It is to be noted however that the appended drawings illustrate only typical embodiments of the invention and are therefore not to be considered limiting of its scope, for the invention may admit to other equally effective embodiments.

DETAILED DESCRIPTION OF THE EMBODIMENTS

Figure 1:
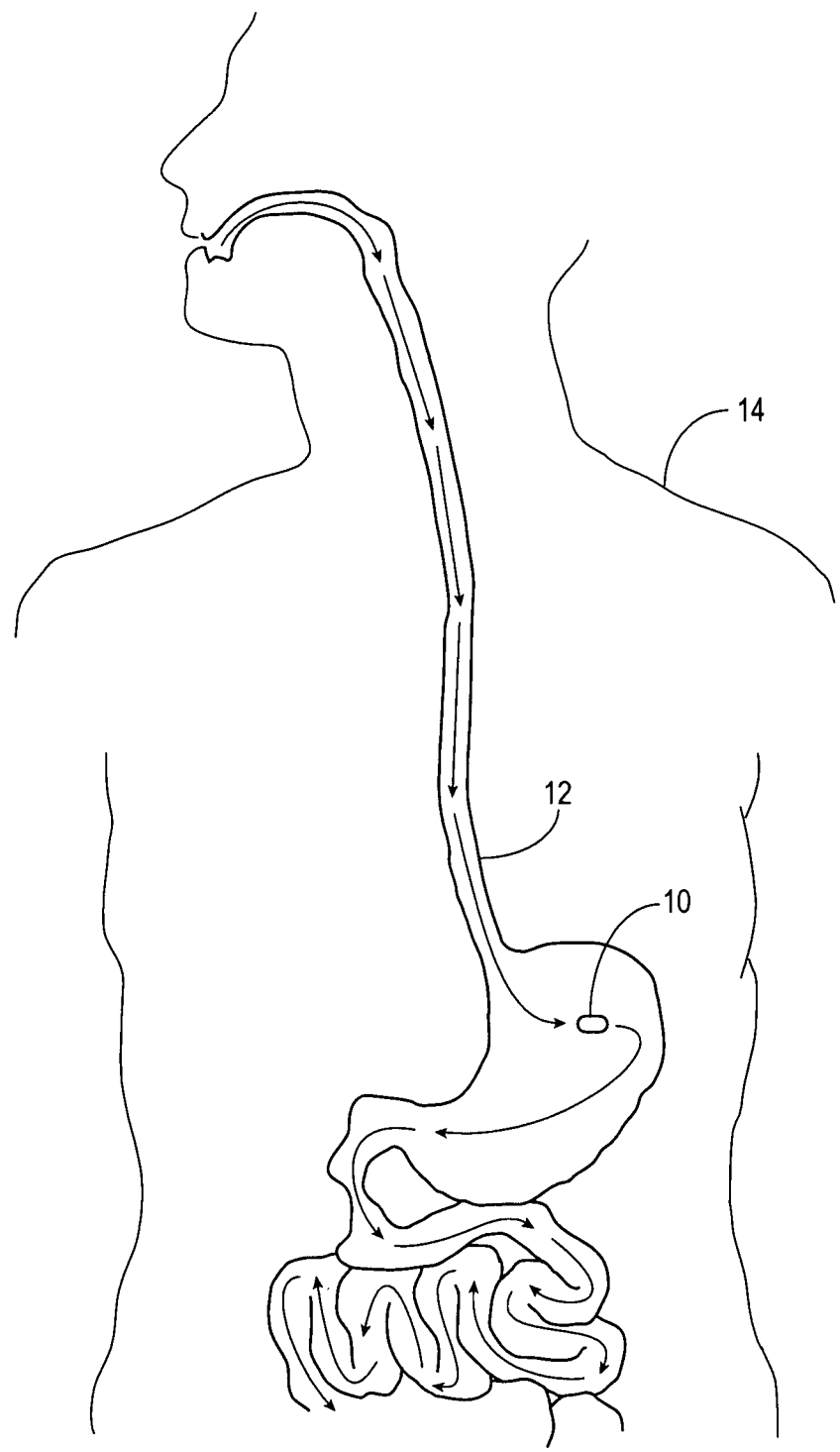
FIG. 1 is a diagrammatic view of a gastrointestinal stimulator device positioned within a gastrointestinal tract of a user in accordance with the present invention.

Present embodiments of the invention are shown in the above-identified figures and described in detail below. In describing the embodiments, like or identical reference numerals are used to identify common or similar elements. The figures are not necessarily to scale and certain features in certain views of the figures may be shown exaggerated in scale or in schematic in the interest of clarity and conciseness.

Referring now to the drawings, and in particular to FIG. 1, shown therein and designated by reference numeral 10 is a gastrointestinal stimulator device (hereinafter referred to as "stimulator device"), constructed in accordance with the present invention, for providing stimulation to a gastrointestinal tract 12 of a user 14. The gastrointestinal tract 12 of a user 14 includes the alimentary canal and organs associated with the alimentary canal such as the stomach, small intestine, large intestine, rectum, and the like. Users 14 may include humans, mammals, or other multicellular organism having a gastrointestinal tract 12.

The stimulator device 10 is placed within the gastrointestinal tract 12 of the user 14, such as by oral administration, rectal administration, administration through any fistula or opening of the gastrointestinal tract, or the like. As the stimulator device 10 travels along and/or through the gastrointestinal tract 12, the stimulator device 10, utilizing any suitable medium, delivers pulses to the gastrointestinal tract 12. Examples of mediums capable of being utilized by the stimulator device 10 include electrical pulses, optical pulses, radiation, acoustic pulses, or the like. Typically, the stimulator device 10 will provide electrical pulses to the gastrointestinal tract 12 as the stimulator device 10 passes through and/or travels along at least a portion of the gastrointestinal tract 12.

In one embodiment, the stimulator device 10 will be programmed prior to administration of the stimulator device 10 into the gastrointestinal tract so that a particular disease or disorder will be treated. In this embodiment, a health care provider or user may be presented with a variety of stimulator devices 10 with each stimulator device 10 preprogrammed to treat a different disorder. Alternatively, the stimulator device 10 can be programmed to treat a particular disorder immediately prior to administration. Alternatively, the stimulator device 10 can be programmed with a variety of different types of treatment regimens for different diseases and/or disorders so that the stimuli can change based upon the location of the stimulator device 10 within the gastrointestinal tract 12.

As discussed above, stimulation of the gastrointestinal tract 12 has been shown to be able to alter, inhibit, or excite gastrointestinal motor functions, activate intrinsic and extrinsic neuronal pathways and/or solicit hormonal/peptide releases. The effects of stimulation on these functions/pathways are related to the selection of stimulation parameters and are believed to have therapeutic potentials for various diseases/disorders. The stimulator device 10 can be used for treating a variety of digestive and eating disorders as well as in use in treating chemotherapy-induced emesis. Exemplary eating disorders include obesity, binging, bulimia, and the like. Gastrointestinal disorders include dysphagia, gastroesophageal reflux diseases, functional dyspepsia, gastroparesis, postoperative ileus, irritable bowel syndrome, constipation, diarrhea, fecal incontinence, pain/discomfort, nausea and vomiting, and the like.

Figure 2:
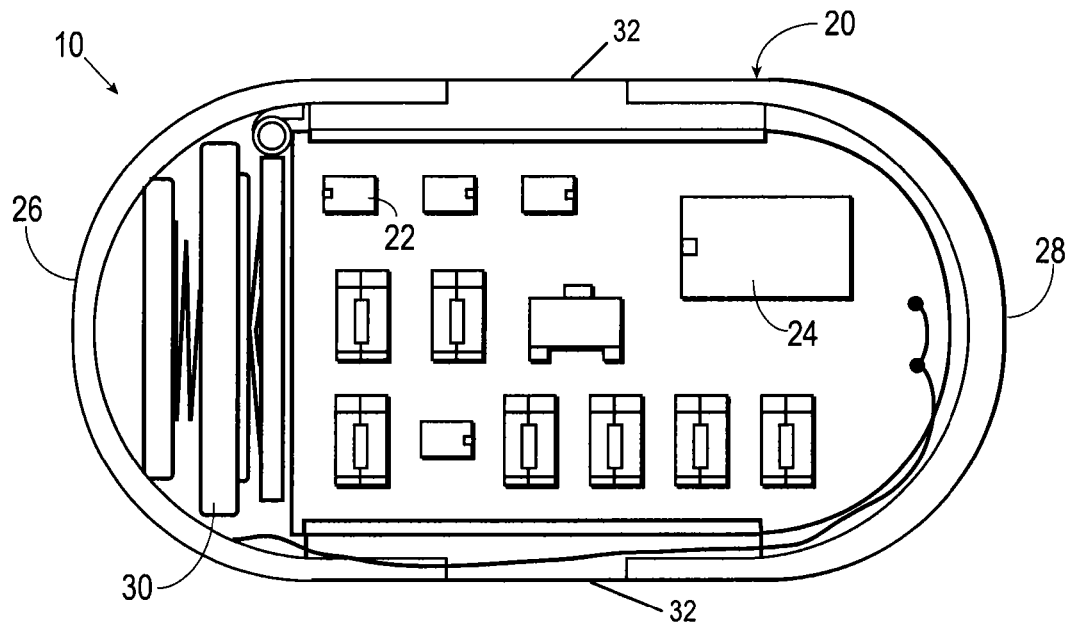
FIG. 2 is a diagrammatic view of one embodiment of a gastrointestinal stimulator device constructed in accordance with the present invention.

Shown in FIG. 2 is a diagrammatic view of one embodiment of the stimulator device 10 constructed in accordance with the present invention. The stimulator device 10 is provided with a housing 20, a pulse generator 22, a controller 24, at least two electrodes 26 and 28, and a power source 30.

The housing 20 is constructed of a biocompatible, non-digestible material transportable through the gastrointestinal tract 12. Examples of biocompatible, non-digestible materials suitable for use in forming the housing are, but not limited to, biocompatible metals, such as unalloyed titanium, wrought titanium alloy, nitrogen austenitic steel, stainless steel, and biocompatible plastic such as polyvinylchloride, polytetrafluoroethelyne, polyethersulfone, polyurethane, polycarbonate, polyetheretherketone and polypropylene.

The housing 20 is sized and shaped to be administered into the gastrointestinal tract 12, such as by oral administration, rectal administration, and the like, and transportable through the at least a portion of the gastrointestinal tract 12. For example, the housing 20 can be shaped in the form of a capsule. However, it should be understood that the housing 20 can be provided in other shapes and/or sizes, so long as the housing 20 can be administered into the gastrointestinal tract 12, and transportable through at least a portion of the gastrointestinal tract 12 preferably without causing any negative side effects, such as irritation. It is also desirable for the housing 20 to be sized and shaped so as not to block the gastrointestinal tract 12 and/or interfere with the operation of the gastrointestinal tract 12. Further, it should be understood that rather than simply being constructed of a biocompatible, non-digestible material, the housing 20 can be formed of a non-biocompatible, or even digestible material that is coated with a biocompatible non-digestible material for transportation through at least a portion of the gastrointestinal tract without causing any negative side effects.

In embodiment depicted in FIG. 2, the housing 20 is formed with the electrodes 26 and 28 separated by an insulating material 32. The electrodes 26 and 28 are connected to the insulating material 32 so as to form a sealed container. The housing 20 defines an interior space containing the pulse generator 22, the controller 24, and the power source 30. However, it should be understood that at least the power source 30, and the controller 24 can be external to the housing 20 so long as the power source 30 and/or controller 24 can communicate and/or provide power, and/or control to the pulse generator 22.

The controller 24 communicates with the pulse generator 22 for controlling the pulses generated by the pulse generator 22. The electrodes 26 and 28 supply a medium containing the pulses generated by the pulse generator 22 to the gastrointestinal tract 12 of the patient/user. As discussed above, the medium can be provided in a variety of forms such as electricity, acoustic waves, radiation, photons, or the like.

The electrodes 26 and 28 can be provided as one or multiple pairs and can be provided on the housing 20 in various locations and different shapes. For example, the electrodes 26 and/or 28 can be provided as a point electrode, a ring electrode, or a patch electrode. The distance between the electrodes 26 and 28 in a pair can also vary.

The controller 24 regulates pulses generated by the pulse generator 22. The controller 24 can be analog, digital, or a combination of both. The controller 24 may be a computer, a microcontroller, a microprocessor, or the like. As shown in FIG. 2, the controller is supported by the housing 20 and is contained within the interior space of the housing 20. The controller 24 can be external to the housing 20 or at least portions of the controller can be external to the housing 20 so long as the controller 24 can communicate with and/or control the pulse generator 22.

The controller 24 uses stimulation parameters to regulate the pulse generator 22 and provide a variety of different types of treatment regimens for different diseases and/or disorders. Stimulation parameters, as discussed in more detail below, may include frequency, pulse width, amplitude, and the like. Programming of the controller 24 can regulate pulses generated by the pulse generator 22 so that can the pulses change based upon the location of the stimulator device 10 within the gastrointestinal tract 12. The controller 24 may be programmed with stimulation parameters prior to administration of the stimulator device 10 into the gastrointestinal tract 12. Alternatively, the controller may be programmed with stimulation parameters during transport of the stimulator device 10 in the gastrointestinal tract 12.

The power source 30, supplies power to the pulse generator 22 and the controller 24. As shown in FIG. 2, the power source 30 is supported by the housing 20. Preferably, the power source 30 is within the internal space of the stimulator device 10. However, it is contemplated that the power source 30 may be located external to the housing 20, provided the power source 30 is in communication with the pulse generator 22 and/or the controller 24. For example, the power source 30 may be provided external to the user 14 through a wireless mechanism, such as inductive loop coupling, electromagnetic control, or the like.

Figure 3:
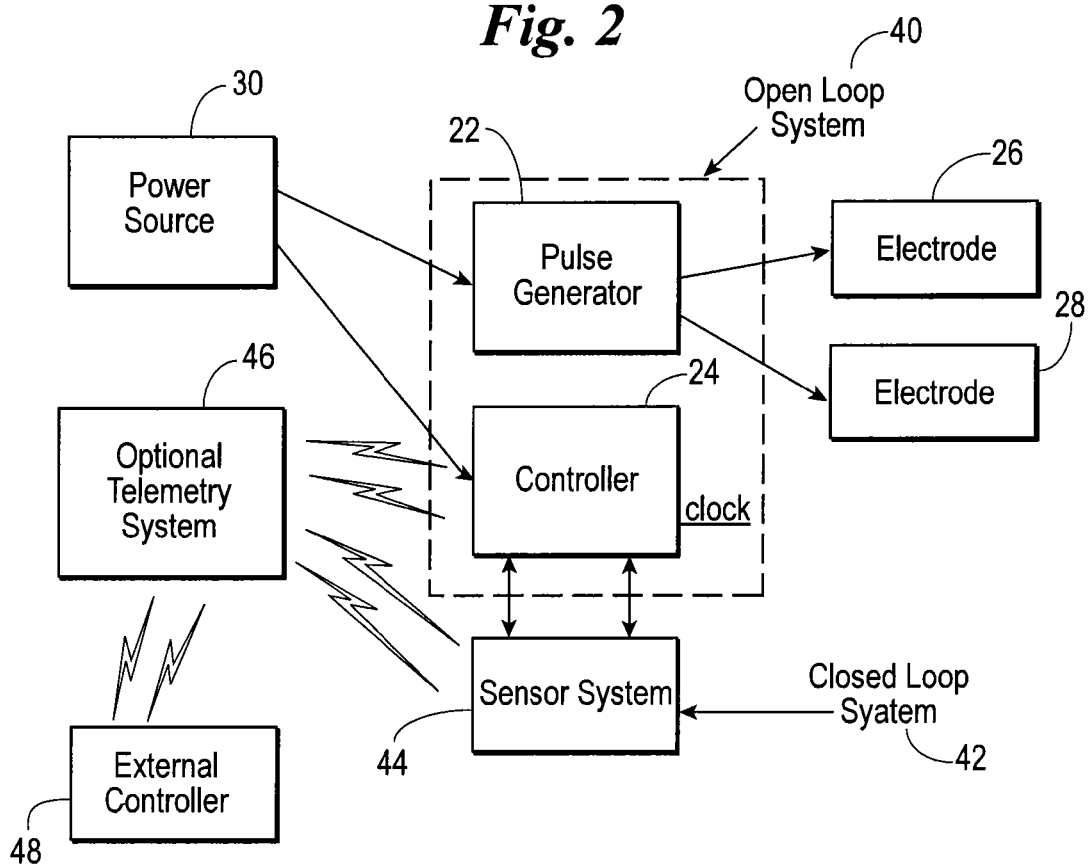
FIG. 3 is a schematic, block diagram of another embodiment of a gastrointestinal stimulator device constructed in accordance with the present invention.

Referring to FIG. 3, regulation of the pulse generator 22 by the controller 24 may include an open-loop system 40, a closed loop system 42, or a combination of the like. In the open loop system 40, pulses are delivered to the electrodes 26 and 28 without the use of sensing inputs such as a sensor system 44. In the closed loop system 42, pulses are delivered to the electrodes 26 and 28 based on inputs to the controller 24 such as mechanical contractions, pressure, tension, electrical signals, temperature, pH or the like from the sensor system 44. Although FIG. 3 shows the controller 24, it should be noted the stimulator device 10 may include the pulse generator 22 supplying pulses to the electrodes 26 and 28 without the use of the controller 24.

One embodiment of the open loop system 40 includes the controller 24, the pulse generator 22, and the electrodes 26 and 28. The controller 24 is in communication with the pulse generator 22 and regulates pulses generated by the pulse generator 22. The pulse generator 22 provides the pulses to the electrodes 26 and 28. The controller 24 may optionally contain a timing mechanism, such as an internal clock, for further controlling the pulses. In another embodiment (not illustrated), the controller 24 is in direct communication with the electrodes 26 and 28 directly and alters the pulses supplied to the gastrointestinal tract by the electrodes 26 and 28 directly.

The closed-loop system 42, as illustrated in FIG. 3, includes the controller 24, the pulse generator 22, the electrodes 26 and 28, and the sensor system 44. The sensor system 44 communicates with the controller 24 and detects environmental conditions external to the housing 20. The environmental conditions can be used to determine the location of the stimulator device 10 within the gastrointestinal tract of the user. The sensor system 44 can include one or more sensors for sensing a variety of different types of environmental factors which may be surrounding the housing 20 of the stimulator device 10. For example, mechanical contractions, pressure, tension, electrical signals, temperature, pH or the like.

The information received from the sensor system 44 is fed back to the controller 24 so that the controller 24 can vary stimulation parameters and regulate pulses generated by the pulse generator 22. For example, the sensor system 44 can detect the location of the stimulator device 10 within the gastrointestinal tract 12 of the user 14 or the effect of its stimulation to the gastrointestinal tract 12. The location or effect of the stimulator device 12 within the user 14 is fed back to the controller 24. The controller 24 then regulates the frequency, duration, and/or amplitude of the pulses generated by the pulse generator 22 based on the location or effect of the stimulator device 10 within the gastrointestinal tract 12 of the user 14. The pulse generator 22 provides the pulses to the electrodes 26 and 28.

The sensor system 44 can also provide a method for synchronized stimulation such that pulses can be provided to the gastrointestinal tract 12 of the user 14 upon detection by the sensor system 44 of a mechanical contraction within the user 14. Synchronizing each pulse with the intrinsic physiological activity of the user 14 may enhance gastrointestinal contractions and accelerate transport of nutrients along the gastrointestinal tract.

As illustrated in FIG. 3, the stimulator device 10 may optionally include a telemetry system 46 that assists in providing external control, external programming, and/or permitting measurement and reporting of information regarding the stimulator device 10 and/or the environmental conditions surrounding the stimulator device 10. The telemetry system provides communication between an internal controller, located within the user 14 such as the sensor system 44 and/or controller 24, while an external controller 48 is external to user. The external controller 48 can be either proximally located to the user 14 or located at a distance to the user 14 so long as the telemetry system can provide communication between the internal controller, such as the sensor system 44 and/or controller 24, and the external controller 48. The communication can be through radio frequency, infrared light, laser light, visible light, acoustic energy, or the like. Both the internal controller and external controller 44 are preprogrammed to provide monitoring, alerting, transmitting, and/or record-keeping of information generated and/or needed for the stimulator device 10.

In one embodiment, communication between the sensor system 44, as the internal controller, and a microprocessor, as the external controller 48, provides monitoring of environmental information surrounding the stimulator device 10 and provides an alerting function if the microprocessor and/or sensor system 44 detect abnormal conditions within the gastrointestinal tract 12 of the user 14. In another embodiment, communication between the sensor system 44, as the internal controller, and the microprocessor, as the external controller 48, allows for the analysis of the environmental information using a decision-making algorithm to provide stimulation parameters. The environmental information is provided by the sensor system 44 and communicated by the telemetry system to the microprocessor. The microprocessor uses the algorithm to determine the stimulation parameters. Such stimulation parameters are communicated again through the telemetry system 46 to either the controller 24 and/or sensor system 44 to regulate the pulses generated by the pulse generator 22.

As previously discussed, stimulation parameters are utilized by the controller 24 to control the pulse generator 22. Stimulation parameters can include frequency, pulse width, amplitude, and the like. The pulses may be intermittent pulses, continuous pulses, and/or trains of intermittent and/or continuous pulses. The controller 24 can vary the stimulation parameters to provide variations in the pulses such that the pulse generator 22 provides long-pulse, short-pulse, dual phase pulses, trains of short-pulses, biphasic trains of pulses, or other variation of pulses. FIGS. 4*a-e* graphically illustrates the relative duration and amplitude of a variety of the exemplary pulses which can be generated by a pulse generator 22 based on the various stimulation parameters provided by the controller 24. It should be understood that the stimulation parameters utilized by the controller 24 can be modified according to the desires of the designer and/or the patient.

Figure 4:
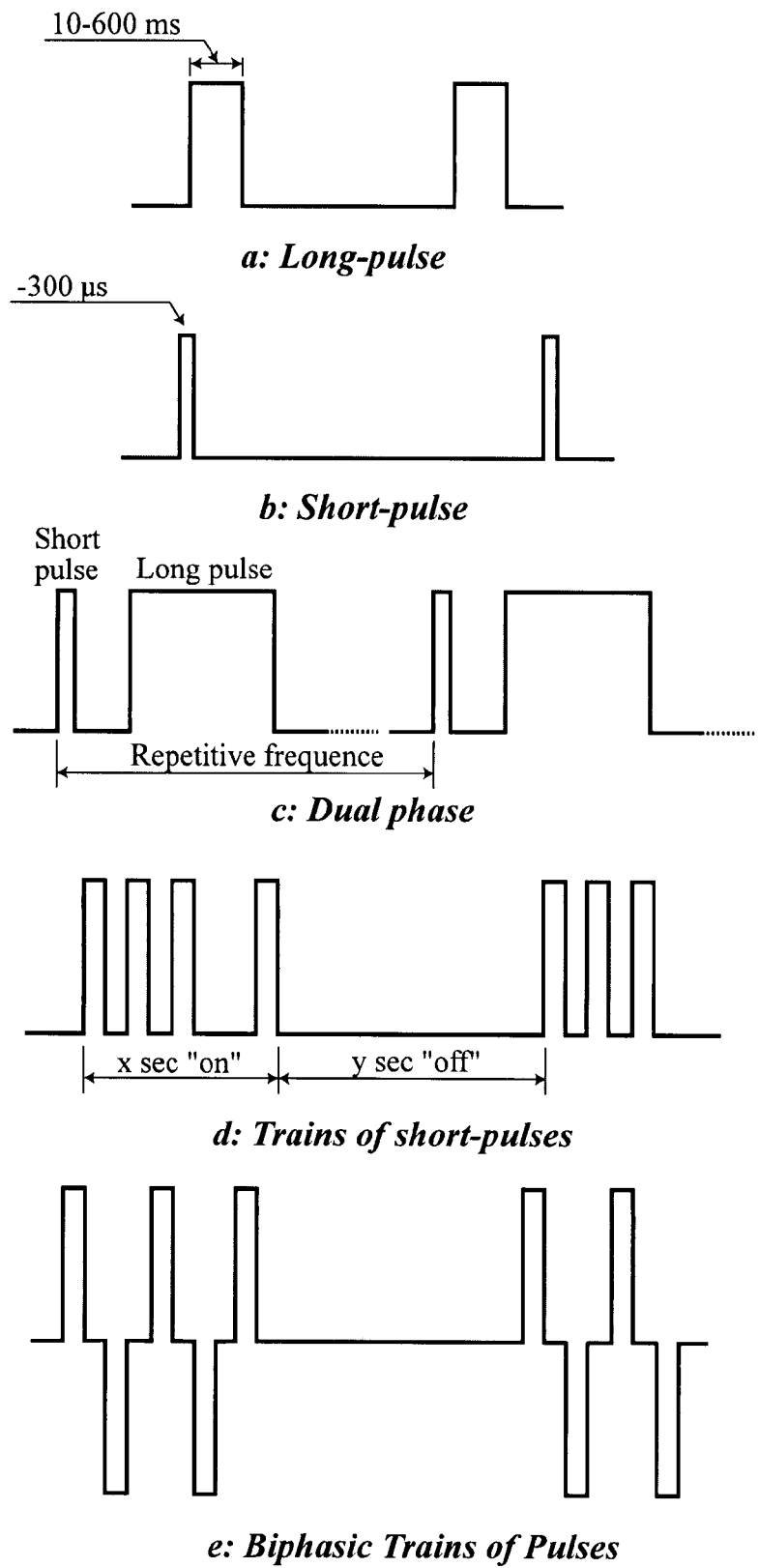
FIGS. 4a-4e illustrate a variety of exemplary pulses which can be generated by a pulse generator of the gastrointestinal stimulator devices and provided to one or more electrode of such gastrointestinal stimulator device for treating a variety of types of gastrointestinal disorders.

FIG. 4*a* graphically illustrates repetitive long-pulses having a pulse width in the order of milliseconds. The long pulse method is able to 'pace' or entrain natural slow waves of the digestive tract. In this method, the electrical stimulus is composed of repetitive single pulses with a pulse width in the order of milliseconds and a stimulation frequency in the vicinity of the physiological frequency of the gastric slow wave as detailed in the article "Systematic review: applications and future of gastric electrical stimulation" by J. Zhang and J. D. Z. Chen in *Alimentary Pharmacology & Therapeutics*, Volume 24, pages 991-1002 (2006) that is hereby incorporated by reference in its entirety.

FIG. 4*b* graphically illustrates repetitive short pulses having a pulse width that is substantially shorter than the long pulse of FIG. 4*a* and is in the order of a few hundred microseconds as opposed to milliseconds. The stimulation frequency is usually a few times higher or substantially higher than the physiological frequency of the gastric slow wave.

FIG. 4*c* graphically illustrates the combining of short pulses and long pulses into a dual phase pulsing. This repetitive pulsing method is composed of one short pulse, or a multitude of short pulses, in the order of a few hundred microseconds, followed by a long pulse, in the order of a few hundred millisecond. Dual phase pulsing has been shown to provide normalizing of gastric dysrhythmia and improvement in the symptoms such as nausea and vomiting. Alternatively, dual phase pulsing may include a long pulse followed by a short pulse, or other combinations of long and short pulses.

FIG. 4*d* graphically illustrates repetitive trains of pulses derived from the combination of two signals. The first signal is a continuous short pulse with a high frequency. The second signal is a control signal to turn the pulses on and off. For example, the second signal can contain a stimulation parameter providing that the duration of the pulse is 'on' for x seconds and 'off' for y seconds. The addition of x and y can then determine the frequency of the pulse train. This kind of stimulation is frequently used in nerve stimulation and other related areas. It should be understood that trains of pulses can include trains of short-pulses, trains of long-pulses, and/or a combination of the both long and short pulses.

FIG. 4*e* graphically illustrates biphasic trains of pulses in which pulse pairs are repeatedly symmetrically generated. The first pulse of each pair has a positive amplitude and the second pulse of each pair has a negative amplitude. Similar to FIG. 4*d*, pulses are repeatedly generated from the combination of two signals. The first signal includes continuous pulse pairs that are repeatedly symmetrically generated. The second signal is a control signal to turn the pulses on and off. For example, the second signal can contain a stimulation parameter providing that the duration of the pulse is 'on' for x seconds and 'off' for y seconds. The addition of x and y can then determine the frequency of the pulse train.

It is contemplated, that in certain applications, it may be beneficial to vary the pulses as the stimulator device 10 travels through at least a portion of the gastrointestinal tract 12 of the user 14. For example, as the stimulator device 10 travels through the gastrointestinal tract, short pulses may be used if the device is used for treating disorders associated with the nervous systems such as pain, nausea and vomiting, long pulses or train of pulses may be used if the device is used for treating disorders associated with the movement of nutrient through the gastrointestinal tract, such as obesity or impaired gastrointestinal motility; a combination of short and long pulses will be used if the device is used to treat disorders affected by both the nervous systems and gastrointestinal motility. Additionally, although a particular pulse may be used throughout travel of the stimulator device 10 in the gastrointestinal tract 12, it may be beneficial to vary the amplitude, frequency, and/or duration of the pulse depending on location of the stimulator device 10 within the gastrointestinal tract 12.

As discussed above, the stimulator device 10 is used to emit a medium for treatment of eating disorders such as obesity or a gastrointestinal disorder or disease, such as dysphagia, gastroesophageal reflux diseases, functional dyspepsia, gastroparesis, postoperative ileus, irritable bowel syndrome, constipation, diarrhea, fecal incontinence, pain/discomfort, nausea and vomiting, obesity, eating disorders as well as in the treatment of chemotherapy-induced emesis. In general, use of the stimulator device 10 includes providing the stimulator device 10 to the user 14. The stimulator device 10 is placed in the gastrointestinal tract 12 of the user 14. Methods of administering the stimulator device 10 within the gastrointestinal tract 12 of the user may include oral administration, such as swallowing of the stimulator device 10, rectal administration, such as the use of a suppository, or other similar mechanisms. The stimulator device 10 need only be placed in the gastrointestinal tract 12 of a user 14 so that the stimulator device 10 can travel through at least a portion of the gastrointestinal tract 12.

Once the stimulator device 10 is inside the gastrointestinal tract 12, the stimulator device 10 delivers pulses to the gastrointestinal tract 12. Such pulses can be intermittent pulses, continuous pulses, and/or trains of intermittent and/or continuous pulses as discussed previously.

It is contemplated that the stimulator device 10 may be distributed in a variety of methods. One method of distribution may include providing the stimulator device 10 to the user 14 by a medical professional. For example, a pharmaceutical distributor can distribute the stimulator device 10 to a medical professional for use in treating gastrointestinal disorders, diseases, and/or for use in chemotherapy-induced emesis. Alternatively, the stimulator device 10 can be distributed to a pharmacy and/or provided to a retailer for over-the-counter distribution to a user 14 for use in treating gastrointestinal disorders, diseases and/or for use in chemotherapy-induced emesis as well as obesity. The pharmacy and/or retailer may then sell the stimulator device 10 directly to the user 14.

The foregoing disclosure includes the best mode for practicing the invention. It is apparent, however, that those skilled in the relevant art will recognize variations of the invention that are not described herein. While the invention is defined by the appended claims, the invention is not limited to the literal meaning of the claims, but also includes these variations.

What is claimed:

1. A method of using a stimulation device for treatment of at least one eating disorder, comprising the steps of:

receiving a stimulation device sized and shaped to be swallowed by a user, wherein the stimulation device includes a pulse generator and at least a pair of electrodes, at least a portion of the pulse generator encapsulated within a housing, the electrodes separated by an insulating material to form the housing; and swallowing the stimulation device, by the user to place the stimulation device in the gastrointestinal tract of the user, to deliver, by the stimulation device, pulses to at least the stomach of the gastrointestinal tract to inhibit gastrointestinal contractions to delay gastric emptying to treat the eating disorder.

2. The method of claim 1, wherein the eating disorder is obesity.

3. The method of claim 1, wherein the eating disorder is bulimia.

4. The method of claim 1, wherein the eating disorder is binge eating.

5. The method of claim 1, further comprising the step of programming a controller in communication with the stimulation device with a stimulation parameter to control at least frequency of the pulses.

6. The method of claim 5, wherein the controller is programmed prior to placement of the stimulation device in the gastrointestinal tract of the patient.

7. The method of claim 1, wherein the stimulation device delivers continuous pulses.

8. The method of claim 1, wherein the stimulation device delivers intermittent pulses.

9. The method of claim 1, wherein the stimulation device delivers a train of pulses.

\* \* \* \* \*